(12) United States Patent
Yeh et al.

(10) Patent No.: US 8,632,199 B2
(45) Date of Patent: Jan. 21, 2014

(54) LAMP APPARATUSES

(75) Inventors: Wen-Yung Yeh, Hsinchu County (TW); Jui-Ying Lin, Taipei (TW); Yu-Chen Yu, Taipei (TW); Ming-Te Lin, Taipei County (TW); Yu-Chun Lin, Hsinchu County (TW); Ta-Wei Chien, Hsinchu (TW)

(73) Assignee: Epistar Corporation, Hsinchu (TW)

( * ) Notice: Subject to any disclaimer, the term of this patent is extended or adjusted under 35 U.S.C. 154(b) by 670 days.

(21) Appl. No.: 12/550,337

(22) Filed: Aug. 28, 2009

(65) Prior Publication Data

US 2009/0316412 A1 Dec. 24, 2009

Related U.S. Application Data

(63) Continuation-in-part of application No. PCT/CN2007/003278, filed on Nov. 20, 2007, and a continuation-in-part of application No. PCT/CN2007/003279, filed on Nov. 20, 2007.

(51) Int. Cl.
*F21V 33/00* (2006.01)

(52) U.S. Cl.
USPC .............................. 362/95; 200/335; 307/141

(58) Field of Classification Search
USPC ................... 362/95, 145–147, 240, 244, 246, 362/249.01, 249.02, 249.05, 249.1, 249.11, 362/249.12, 276, 311.02, 363, 394, 395, 362/800, 802; 200/61.85, 332, 33 R, 41, 200/335, 543, 546, 562; 307/139, 141
See application file for complete search history.

(56) References Cited

U.S. PATENT DOCUMENTS

| | | | |
|---|---|---|---|
| 2,848,585 A * | 8/1958 | Atkin | 200/331 |
| 5,306,957 A * | 4/1994 | Ellingham et al. | 307/141 |
| 2002/0117376 A1 | 8/2002 | Cheng | |
| 2006/0044864 A1 | 3/2006 | Lin et al. | |
| 2006/0209569 A1 * | 9/2006 | Yuen | 362/641 |
| 2006/0256826 A1 | 11/2006 | Lin et al. | |
| 2007/0131942 A1 | 6/2007 | Yen et al. | |
| 2007/0133230 A1 | 6/2007 | Lin | |
| 2007/0138495 A1 | 6/2007 | Lin et al. | |

FOREIGN PATENT DOCUMENTS

| | | |
|---|---|---|
| CN | 2562773 Y | 7/2003 |
| CN | 2722021 Y | 8/2005 |
| CN | 1886017 A | 12/2006 |
| CN | 101021304 A | 8/2007 |
| TW | M210479 | 8/1993 |

* cited by examiner

*Primary Examiner* — Hargobind S Sawhney
(74) *Attorney, Agent, or Firm* — Bacon & Thomas, PLLC

(57) ABSTRACT

A lamp apparatus include a lamp body, at least an alternating current light-emitting diode and a plug. The alternating current light-emitting diode is disposed on a lamp body. The plug is electrically connected to the alternating current light-emitting diode. In lamp apparatuses utilizing AC LED, heat generated thereby is almost concentrated on chips. Compared with conventional lamp apparatuses utilizing DC LEDs, heat generated thereby is distributed on chips and outer rectifier. In lamp apparatuses utilizing AC LEDs, heat generated thereby is almost concentrated on chips because AC LEDs operate directly with AC electric power, omitting a rectifier and preventing power loss during operation of power rectification. Therefore, the heat accumulated on the chips of the AC LEDs is enough to be used to evaporate essential oil. In another embodiment, the invention utilizes low-resistance pure water surrounding the AC LED to dissipate its heat.

20 Claims, 8 Drawing Sheets

LAMP APPARATUSES

CROSS REFERENCE TO RELATED APPLICATIONS

This Application is a continuation-in-part application of PCT Application No. PCT/CN2007/003278, filed on Nov. 20, 2007, and PCT Application No. PCT/CN2007/003279, filed on Nov. 20, 2007, the entireties of which are incorporated by reference herein.

BACKGROUND OF THE INVENTION

1. Field of the Invention

The invention relates to lamp apparatuses, and more particularly to lamp apparatuses with alternating current light-emitting diodes.

2. Description of the Related Art

Most lamp apparatuses use direct current light-emitting diodes (DC LEDs) as light sources. As public power supply is provided with alternating current (AC) electric power, rectifiers are required for the lamp apparatuses to rectify the AC electric power into direct current (DC) electric power, enabling the DC LEDs to radiate. Accordingly, when the lamp apparatus is applied to AC electric power, two operations of power transformation must be performed. The first operation of power transformation is rectifying the AC electric power into the DC electric power using the rectifiers. The second operation of power transformation is transforming the DC electric power into light by the DC LEDs. Generally speaking, the efficiency of the first operation of the power transformation is low and consumes tremendous power, thus causing the DC LEDs to provide low radiation efficiency. Therefore, the first operation of power transformation often generates more heat than the second operation of power transformation does.

Moreover, US 2002/0117376 discloses an essential oil evaporator applying a DC LED as a light source. Because most the heat of the DC LED generated most in the first operation as described above, the heat is mainly distributed on a rectifier. The heat accumulated on the chip is not sufficient to heat or evaporate the essential oil. Therefore, in this patent, the DC LED simply provides functions of decoration or illumination and is used for evaporating the essential oil. The essential oil is evaporated by a heater.

Hence, there is a need for a lamp apparatus applying a light source, which can generate enough heat to evaporate essential oil.

Given the fast paced lifestyle for most people, items are often misplaced at home or at the workplace. For example, after returning home, a person might randomly place down their keys. The keys are not placed in a specific location. When leaving home, the person has trouble remembering where they may have placed their keys and cannot easily find the keys.

Hence, there is a need for a lamp apparatuses providing functions of highlighting the location of an object and decorating the object.

BRIEF SUMMARY OF THE INVENTION

An exemplary embodiment of the invention provides a lamp apparatus comprising a base, a circuit board, an alternating current light-emitting diode, a plug, and a hook arm. The circuit board is disposed in the base and comprises an actuation switch. The alternating current light-emitting diode is connected to the circuit board. The plug is electrically connected to the circuit board. The hook arm pivots the base and switches between a first position and a second position. When an object is hung on the hook arm and the hook arm switches to the first position, the hook arm separates from the actuation switch and the actuation switch enables the alternating current light-emitting diode to operate in a first operational mode. When the hook arm switches to the second position, the hook arm abuts the actuation switch and the actuation switch enables the alternating current light-emitting diode to operate in a second operational mode.

Another exemplary embodiment of the invention provides a lamp apparatus comprising a base, a circuit board, an alternating current light-emitting diode, a plug, and a hook arm. The circuit board is disposed in the base. The alternating current light-emitting diode is connected to the circuit board. The plug is electrically connected to the circuit board. The hook arm is connected to the base and comprises a touch sensor electrically connected to the circuit board. When contacting an object, the touch sensor enables the alternating current light-emitting diode to operate in a first operational mode. When separating from the object, the touch sensor enables the alternating current light-emitting diode to operate in a second operational mode.

BRIEF DESCRIPTION OF THE DRAWINGS

The invention could be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Compared with conventional lamp apparatuses utilizing DC LEDs, heat generated thereby is distributed on chips and outer rectifier. In lamp apparatuses utilizing AC LEDs, heat generated thereby is almost concentrated on chips because AC LEDs operate directly with AC electric power, omitting a rectifier and preventing power loss during operation of power rectification. Therefore, the heat accumulated on the chips of the AC LEDs is enough to be used to evaporate essential oil. In another embodiment, the invention utilizes low-resistance pure water surrounding the AC LED to dissipate its heat. In still another embodiment, the invention utilizes metal-made support stand to dissipate heat.

First Embodiment

Figure 1:
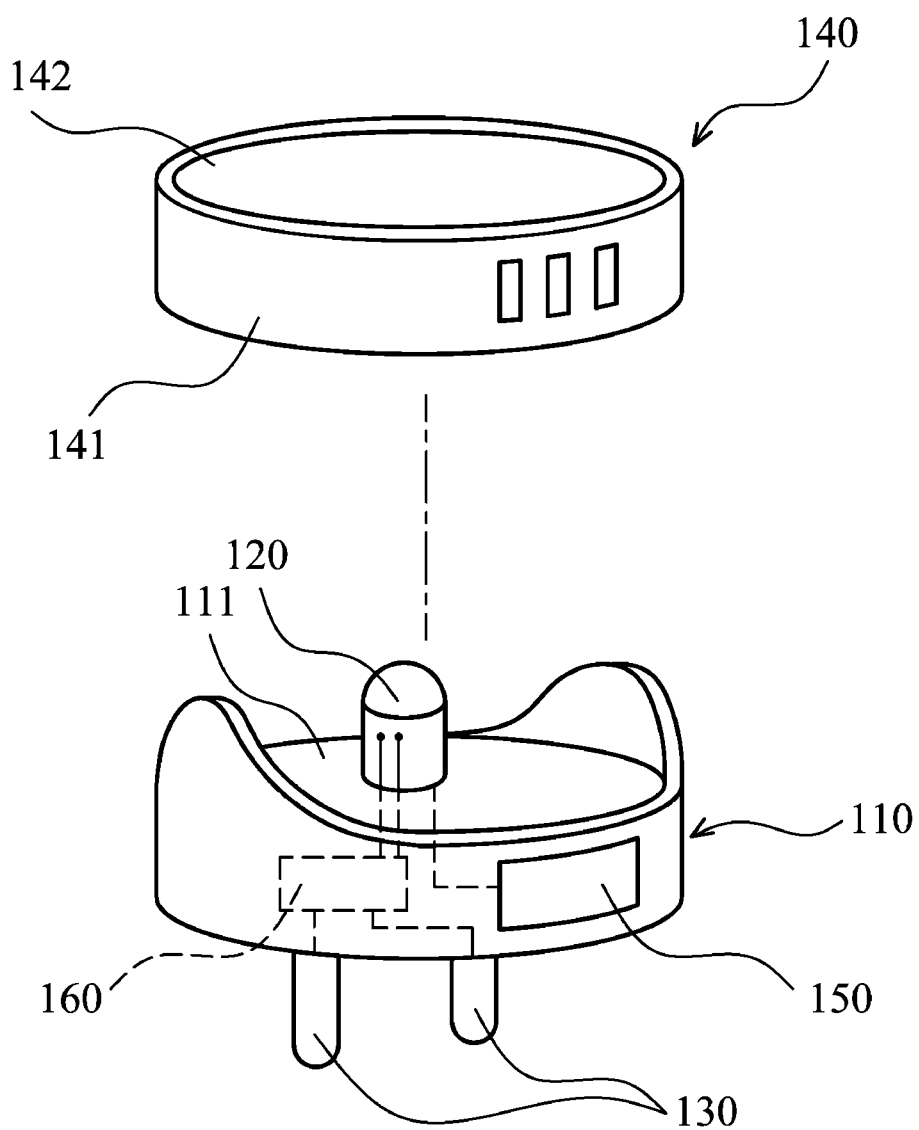
FIG. 1 is a schematic exploded perspective view of a lamp apparatus of a first embodiment of the invention.

Referring to FIG. 1, a lamp apparatus 101 serves as an essential oil evaporator and comprises a lamp body 110, an alternating current light-emitting diode (AC LED) 120, a plug 130, a container 140, a heating adjustment controller 150, and a temperature overload protection circuit 160.

The lamp body 110 comprises a heat-conductive surface 111.

The alternating current light-emitting diode 120 is disposed on the lamp body 110. Specifically, the alternating current light-emitting diode 120 is disposed on the heat-conductive surface 111 of the lamp body 110. In a preferred embodiment, the alternating current light-emitting diode 120 is directly connected to the heat-conductive surface.

The plug 130 is electrically connected to the alternating current light-emitting diode 120. In a preferred embodiment, the plug 130 is integrated with the lamp body 110 and is disposed on the opposite surface of the heat-conductive surface 111 of the lamp body 110. In a more preferred embodiment, the plug 130 could be a European-type plug.

The container 140 is disposed on the lamp body 110 and could be used to contain a fluid, such as essential oil or water. Specifically, the container 140 comprises heat-conductive material. Moreover, the container 140 comprises a cup 141 and a cover 142. The cup 141 is disposed on the lamp body 110 and could be used to contain the essential oil or water. The cover 142 is disposed on the cup 141 and is substantially transparent or semi-transparent. Specifically, the alternating current light-emitting diode 120 is near the (cup 141 of the) container 140, or/and the heat-conductive surface 111 of the lamp body 110 is near the (cup 141 of the) container 140.

The heating adjustment controller 150 is electrically connected to the alternating current light-emitting diode 120. In a preferred embodiment, the heating adjustment controller 150 is on a surface of the lamp body 110.

The temperature overload protection circuit 160 is electrically connected between the plug 130 and the alternating current light-emitting diode 120.

Accordingly, when the plug 130 of the lamp apparatus 101 is put in a socket (not shown) to be supplied with the AC electric power, the alternating current light-emitting diode 120 radiates and generates heat. In a preferred embodiment, the cup 141 and the essential oil therein are substantially transparent or semi-transparent. At this point, light emitted from the alternating current light-emitting diode 120 passes through the essential oil in the cup 141, and heat generated by the alternating current light-emitting diode 120 heats and evaporates the essential oil. Compared to a direct current light-emitting diode, an alternating current light-emitting diode has no rectifier and the heat generated mainly from chip, not from rectifier. More heat is accumulated on the chip of the alternating current light-emitting diode than on the chip of the direct current light emitting diode. Therefore, the alternating current light-emitting diode is a good means to evaporate essential oil. However, in general condition, the chip of the direct current light-emitting diode can't be used to as a heating means to evaluate essential oil. Specifically, when the alternating current light-emitting diode 120 is near the (cup 141 of the) container 140 and the container 140 is made of heat-conductive material, the heat generated from the alternating current light-emitting diode 140 thereby heats and evaporates the essential oil through the (cup 141 of the) container 140. In another embodiment, the heating means used to evaporate the essential oil could be more than one alternating current light-emitting diode. Namely, the lamp apparatus 101 may selectively comprise a plurality of alternating current light-emitting diodes surrounding or near the (cup 141 of the) container 140 to achieve the same heating function. In another aspect, the alternating current light-emitting diode 120 is connected and contacted with the heat-conductive surface 111 of the lamp body 110. The heat-conductive surface 111 is near the (cup 141 of the) container 140, more preferably, the heat-conductive surface 111 is connected and directly contact with the (cup 141 of the) container 140, the heat generated by the alternating current light-emitting diode 120 is transmitted to the (cup 141 of the) container 140 through the heat-conductive surface 111, heating and evaporating the essential oil.

Accordingly, as the cover 142 of the container 140 is substantially transparent or semi-transparent, the level of the essential oil in the cup 141 could be visually examined. A user can thus decide whether or not to replenish the cup 141 with additional essential oil.

Moreover, the lamp apparatus 101 can provide different modes of radiation or heating by means of the heating adjustment controller 150. Namely, the heating adjustment controller 150 can control intensity of the light output from the alternating current light-emitting diode 120 and evaporation rate of the essential oil. For example, during resting time, the user can reduce the intensity of the light output from the alternating current light-emitting diode 120 using the heating adjustment controller 150. At this point, the amount of the heat generated by the alternating current light-emitting diode 120 is also reduced, thus reducing the evaporation rate of the essential oil. On the other hand, during day time, the user can increase the intensity of the light output from the alternating current light-emitting diode 120 using the heating adjustment controller 150. Meanwhile, the amount of the heat generated by the alternating current light-emitting diode 120 is also increased, thus increasing the evaporation rate of the essential oil.

Additionally, when the temperature of the essential oil in the cup 141 is excessively high, the temperature overload protection circuit 160 electrically connected between the plug 130 and the alternating current light-emitting diode 120 cuts off the AC electric power supplied to the alternating current light-emitting diode 120, protecting the lamp apparatus 101 from damage due to the excessively high temperature of the essential oil.

Second Embodiment

Elements corresponding to those in the first embodiment share the same reference numerals.

Figure 2:
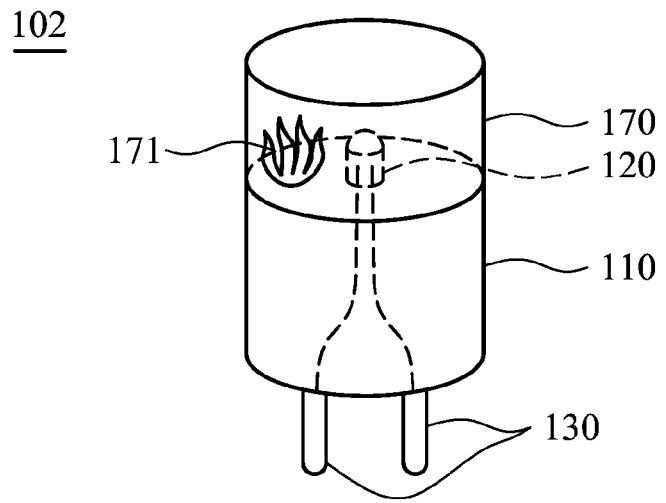
FIG. 2 is a schematic perspective view of a lamp apparatus of a second embodiment of the invention.

Referring to FIG. 2, a lamp apparatus 102 comprises a lamp body 110, an alternating current light-emitting diode 120, a plug 130, and a lampshade 170.

The lampshade 170 covers the alternating current light-emitting diode 120. In a preferred embodiment, the lampshade 170 could be connected to the lamp body 110. Additionally, the lampshade 170 could be substantially transparent or semi-transparent to let all or a part of the light generated from the alternating current light-emitting diode 120 pass through. In this embodiment, the lampshade 170 comprises at least one pattern 171 formed thereon.

Structure, disposition, and function of other elements in this embodiment are the same as those in the first embodiment, and explanation thereof is omitted for simplicity.

When the plug 130 of the lamp apparatus 102 is put in a socket to be applied to the AC electric power, the pattern 171 on the lampshade 170 is projected to the exterior thereof by the alternating current light-emitting diode 120. For example, the pattern 171 on the lampshade 170 could be projected onto a wall (not shown) by radiation of the alternating current light-emitting diode 120, achieving a decorative effect.

Third Embodiment

Elements corresponding to those in the first embodiment share the same reference numerals.

Figure 3:
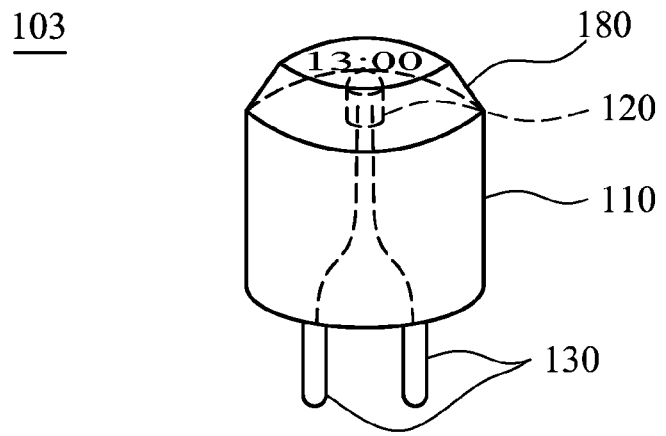
FIG. 3 is a schematic perspective view of a lamp apparatus of a third embodiment of the invention.

Referring to FIG. 3, a lamp apparatus 103 comprises a lamp body 110, an alternating current light-emitting diode 120, a plug 130, and a timepiece 180.

The timepiece 180 is adjacent to the alternating current light-emitting diode 120.

Structure, disposition, and function of other elements in this embodiment are the same as those in the first embodiment, and explanation thereof is omitted for simplicity.

When the plug 130 of the lamp apparatus 103 is put in a socket to be applied to the AC electric power, time provided by the timepiece 180 is projected to the exterior of the lamp body 110 by the alternating current light-emitting diode 120. For example, the time pattern provided by the timepiece 180 could be projected onto a wall by radiation of the alternating current light-emitting diode 120.

Fourth Embodiment

Elements corresponding to those in the first embodiment share the same reference numerals.

Figure 4:
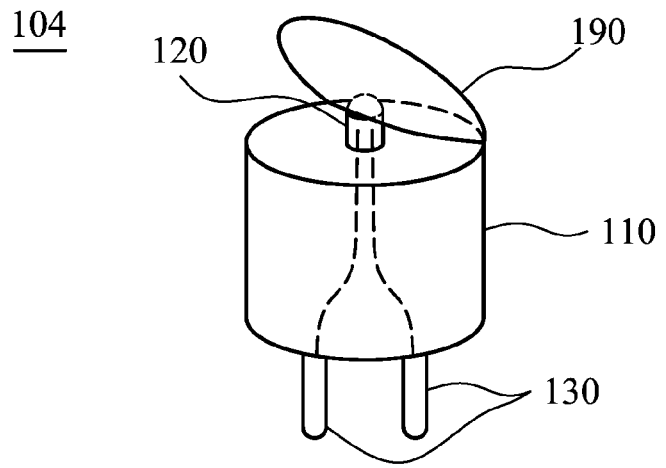
FIG. 4 is a schematic perspective view of a lamp apparatus of a fourth embodiment of the invention.

Referring to FIG. 4, a lamp apparatus 104 comprises a lamp body 110, an alternating current light-emitting diode 120, a plug 130, and a reflector 190.

The reflector 190 is adjacent to the alternating current light-emitting diode 120, reflecting light output thereby. Specifically, the reflector 190 is rotatably connected to the lamp body 110. Accordingly, by adjustment of an angle between the reflector 190 and the lamp body 110, the light output by the alternating current light-emitting diode 120 could be reflected in different directions.

Structure, disposition, and function of other elements in this embodiment are the same as those in the first embodiment, and explanation thereof is omitted for simplicity.

Fifth Embodiment

Figure 5:
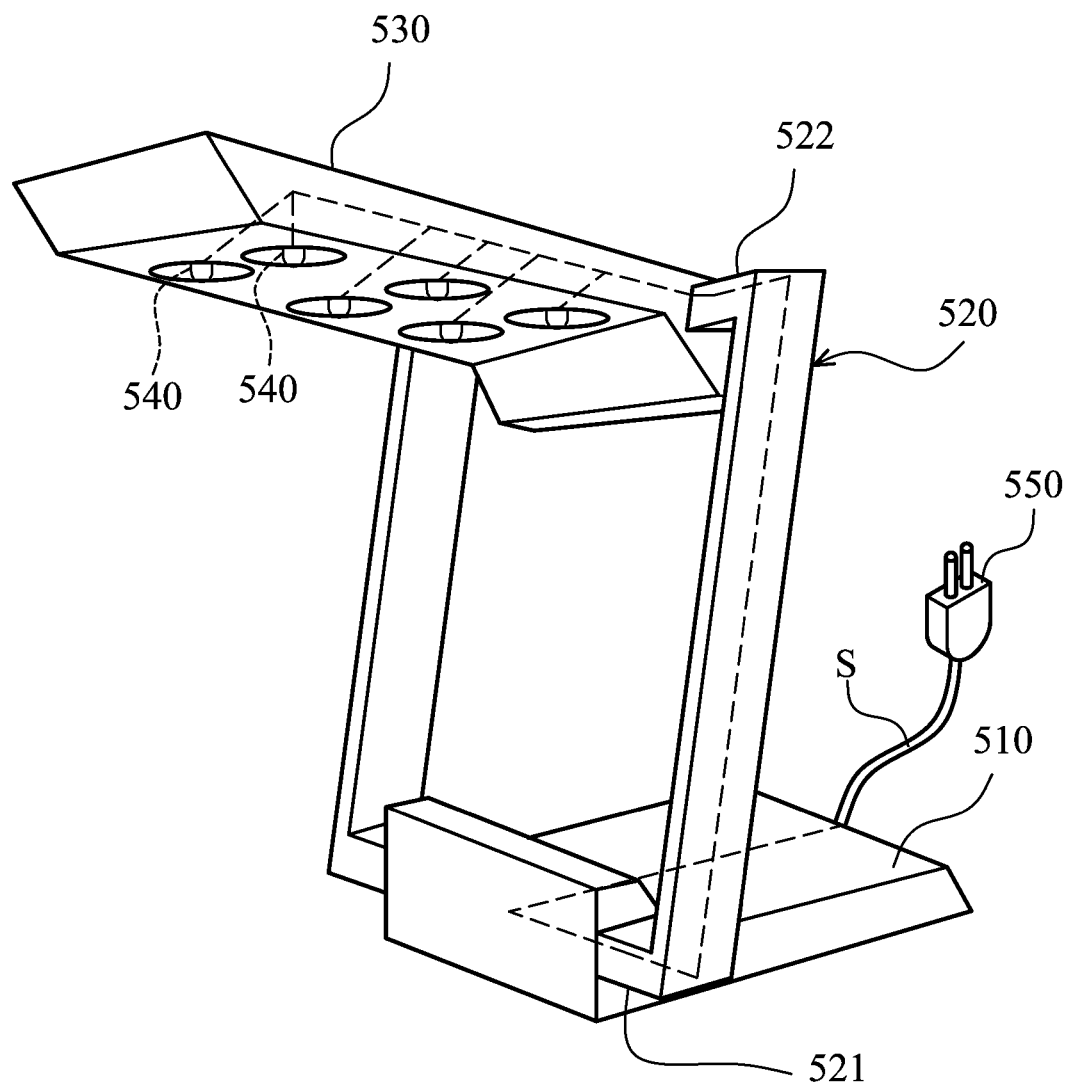
FIG. 5 is a schematic perspective view of a lamp apparatus of a fifth embodiment of the invention.

Referring to FIG. 5, a lamp apparatus 500 comprises a base 510, a support stand 520, a lamp body 530, a plurality of alternating current light-emitting diodes 540, and a plug 550.

The support stand 520 comprises a first end 521 and a second end 522 opposite thereto. The support stand 520 is rotatably connected to the base 510 by the first end 521.

The lamp body 530 is rotatably connected to the second end 522 of the support stand 520. Therefore, the angle between the lamp body 530 and the support stand 520 is adjustable to adjust the illuminating angle and the illuminating area of the alternating current light-emitting diodes 540.

The alternating current light-emitting diodes 540 are disposed on the lamp body 530.

The plug 550 is electrically connected to the alternating current light-emitting diodes 540. Specifically, the plug 550 is electrically connected to the alternating current light-emitting diodes 540 via a power cable S or wire line.

When the plug 550 of the lamp apparatus 500 is put in a socket to be supplied with the AC electric power, the alternating current light-emitting diodes 540 radiate. Moreover, by adjusting a relative rotating position between the lamp body 530 and the support stand 520 and/or that between the support stand 520 and the base 510, the direction of radiation of the alternating current light-emitting diodes 540 could be adjusted. Additionally, the lamp apparatus 500 could be folded by simultaneously adjusting the relative rotating positions between the lamp body 530 and the support stand 520 and between the support stand 520 and the base 510.

Sixth Embodiment

Figure 6:
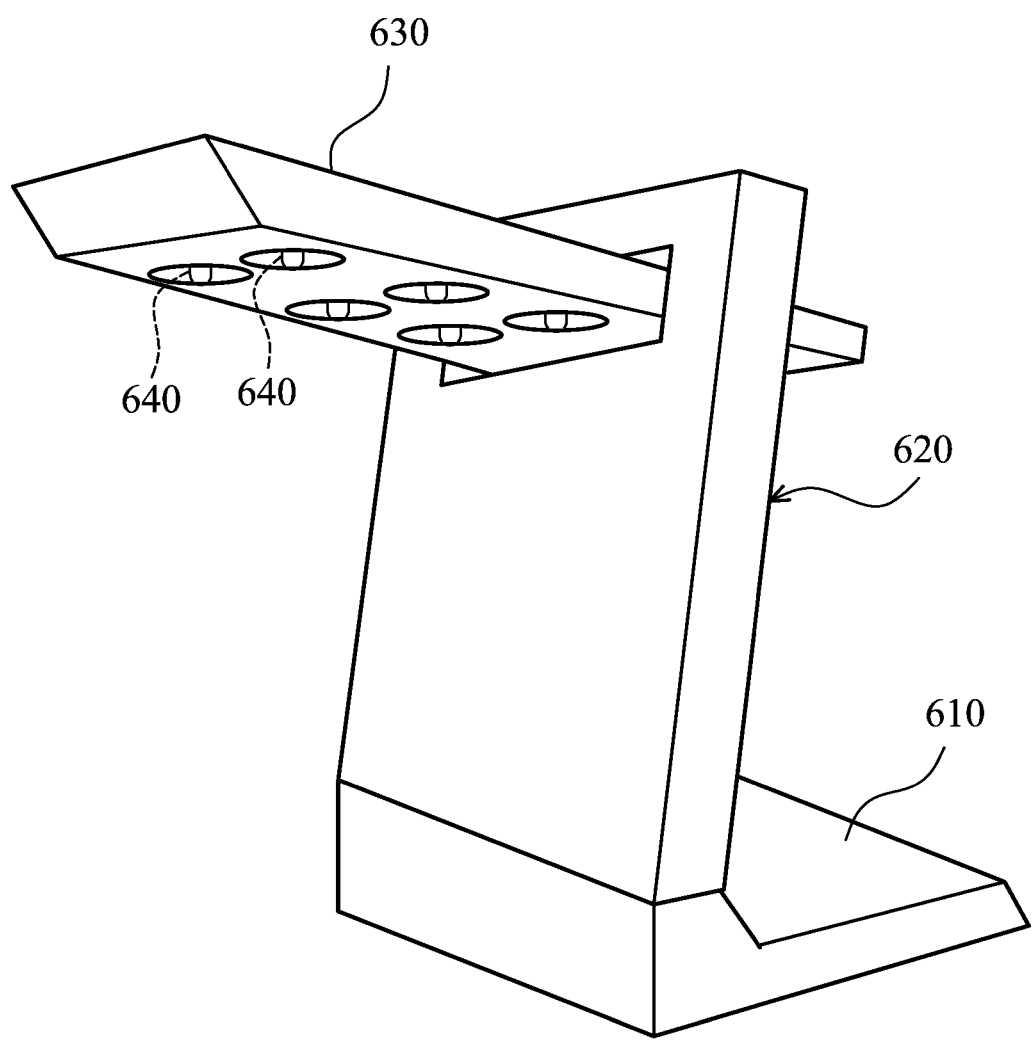
FIG. 6 is a schematic perspective view of a lamp apparatus of a sixth embodiment of the invention.

Referring to FIG. 6, a lamp apparatus 600 comprises a base 610, a support stand 620, a lamp body 630 and a plurality of alternating current light-emitting diodes 640.

The support stand 620 is connected to the base 610.

The lamp body 630 is rotatably connected to the support stand 620. Therefore, the angle between the lamp body 630 and the support stand 620 is adjustable to adjust the illuminating angle and the illuminating area of the alternating current light-emitting diodes 640.

The alternating current light-emitting diodes 640 are disposed on the lamp body 630.

By adjusting a relative rotating position between the lamp body 630 and the support stand 620, the direction of radiation of the alternating current light-emitting diodes 640 could be adjusted.

In this embodiment, the support stand 620 is made of metal. The heat generated from alternating current light-emitting diode 640 can be dissipated by utilizing the large surface area of the support stand 620. Moreover, the heat dissipation efficiency can further be improved by utilizing the metal housing of the base 610 and the lamp body 630. Because of the improvement of the high heat dissipation efficiency, the life time and the light-emitting efficiency of the alternating current light-emitting diodes 640 are increased.

Seventh Embodiment

Figure 7:
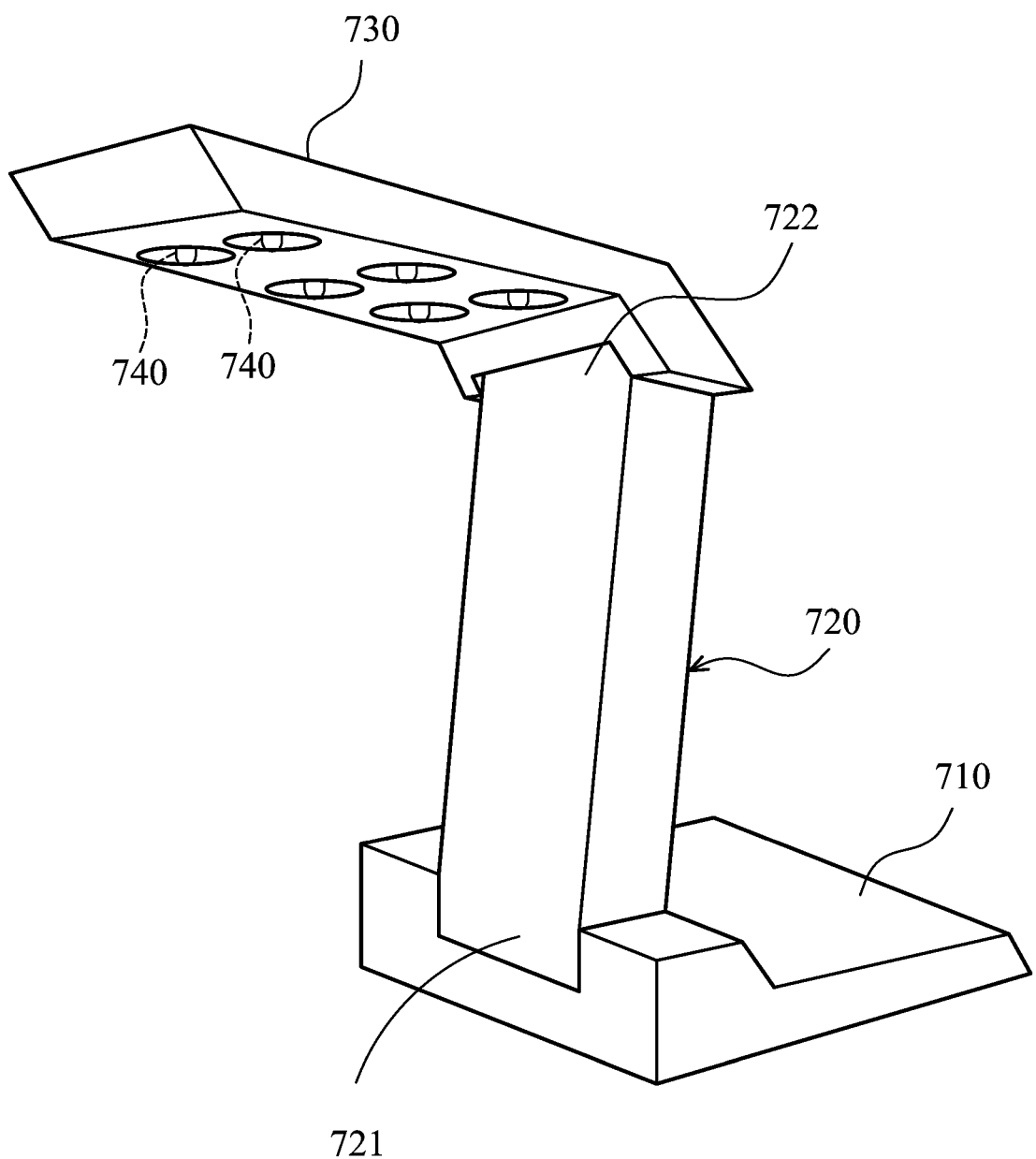
FIG. 7 is a schematic perspective view of a lamp apparatus of a seventh embodiment of the invention.

Referring to FIG. 7, a lamp apparatus 700 comprises a base 710, a support stand 720, a lamp body 730 and a plurality of alternating current light-emitting diodes 740.

The support stand 720 comprises a first end 721 and a second end 722 opposite thereto. The support stand 720 is rotatably connected to the base 710 by the first end 721.

The lamp body 730 is rotatably connected to the second end 722 of the support stand 720. Therefore, the angle between the lamp body 730 and the support stand 720 is adjustable to adjust the illuminating angle and the illuminating area of the alternating current light-emitting diodes 740.

The alternating current light-emitting diodes 740 are disposed on the lamp body 730.

By adjusting a relative rotating position between the lamp body 730 and the support stand 720 and/or that between the support stand 720 and the base 710, the direction of radiation of the alternating current light-emitting diodes 740 could be adjusted. Additionally, the lamp apparatus 700 could be folded by simultaneously adjusting the relative rotating positions between the lamp body 730 and the support stand 720 and between the support stand 720 and the base 710.

In this embodiment, the support stand 720 is made of metal. The heat generated from alternating current light-emitting diode 740 can be dissipated by utilizing the large surface area of the support stand 720. Moreover, the heat dissipation efficiency can further be improved by utilizing the metal housing of the base 710 and the lamp body 730. Because of the high heat dissipation efficiency, the life time and the light-emitting efficiency of the alternating current light-emitting diodes 740 are increased.

Eighth Embodiment

Figure 8:
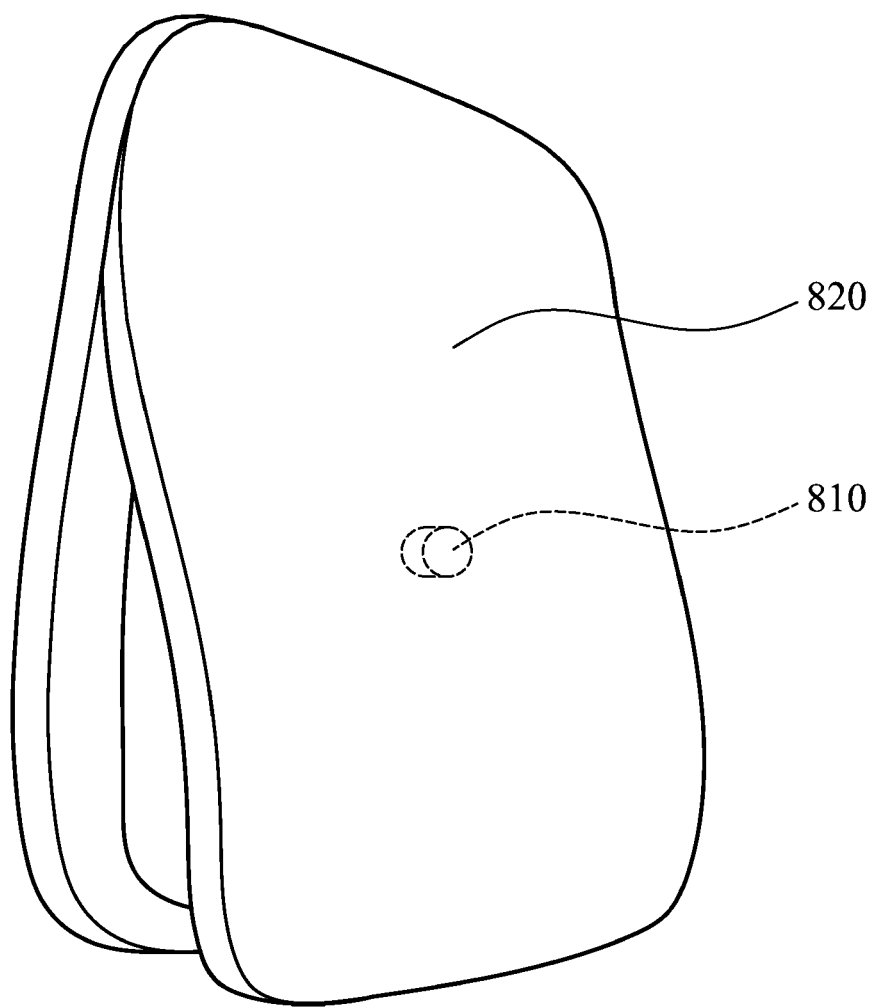
FIG. 8 is a schematic perspective view of a lamp apparatus of an eighth embodiment of the invention.

FIG. 8 shows a lamp apparatus 800 of an eighth embodiment of the invention, which comprises alternating current light-emitting diode 810 and a water layer 820 surrounding the alternating current light-emitting diode 810 to dissipate heat. The water layer 820 is used like a lampshade. Because the water layer 820 is transparent or semitransparent, the light generated from the alternating current light-emitting diodes 810 can pass through them to be blurred. Therefore, the water layer 820 could create special illuminating effect.

Ninth Embodiment

Figure 9A:
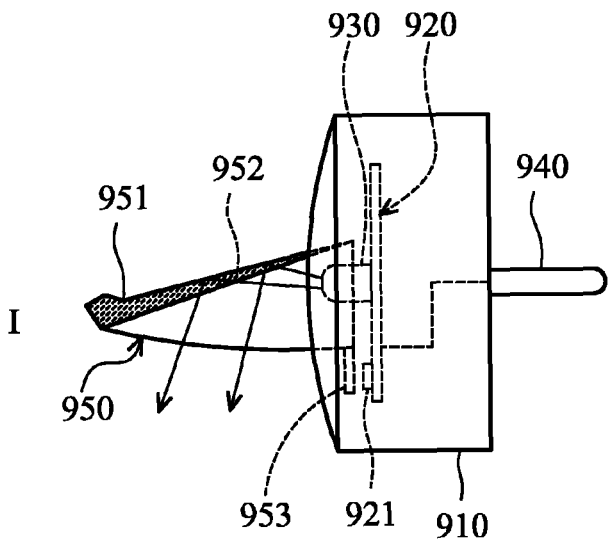
FIG. 9A is a schematic plane view of a lamp apparatus of a ninth embodiment of the invention in an operational mode.
Figure 9B:
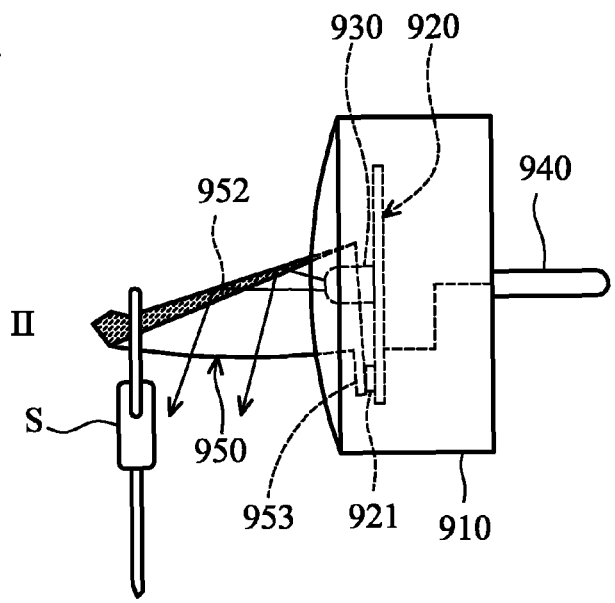
FIG. 9B is a schematic plane view of a lamp apparatus of the ninth embodiment of the invention in another operational mode.
Figure 10:
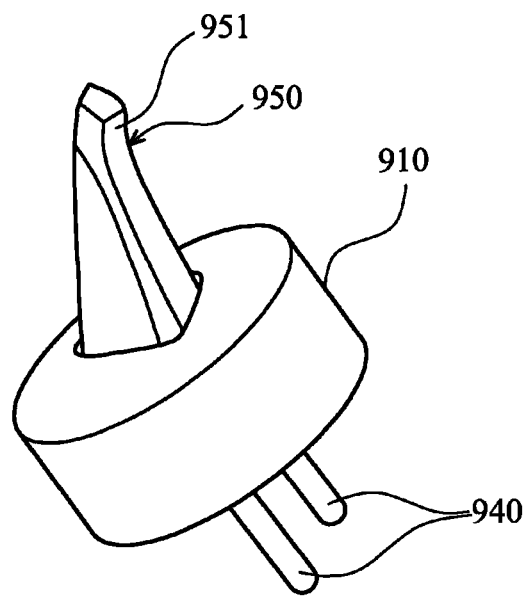
FIG. 10 is a schematic perspective view of the lamp apparatus of the ninth embodiment of the invention.

Referring to FIGS. 9A, 9B, and 10, a lamp apparatus 901 comprises a base 910, a circuit board 920, a alternating current light-emitting diode 930, a plug 940, and a hook arm 950.

In this embodiment, the alternating current light-emitting diode 930 is disposed in the base 910. The base 910 is designed to be substantially transparent or semi-transparent. Therefore, the light emitted from the alternating current light-emitting diode 930 could be transmitted to the exterior of the base 910. In other embodiment, the alternating current light-emitting diode 930 may protrude from the surface of the base 910 and not be disposed in the base 910. Therefore, the base 910 may not need to be substantially transparent or semi-transparent to let the light pass through.

As shown in FIG. 9A and FIG. 9B, the circuit board 920 is disposed in the base 910 and comprises an actuation switch 921.

The alternating current light-emitting diode 930 is connected to the circuit board 920.

The plug 940 is disposed on another surface, opposite to the hook arm 950, of the base 910 and is electrically connected to the circuit board 920. In this embodiment, the plug 940 can be put in a socket (not shown) to acquire AC electric power. Because the alternating current light-emitting diode 930 doesn't need a rectifier, the overall size of the lamp apparatus 901 can be reduced. In a preferred embodiment, the plug 940 could be a European-type plug, the size of the lamp apparatus 901 can be reduced to fix into the space of the recess of a plug-in on a wall. The outer surface of the base 910 of the lamp apparatus 901 is coplanar with the wall surface to achieve an aesthetically pleasing appearance.

The hook arm 950 pivots the base 910 and switches between a first position I (as shown by FIG. 9A) and a second position II (as shown by FIG. 9B). In this embodiment, the hook arm 950 protrudes from the base 910 and could be substantially transparent or semi-transparent. The light emitted from the alternating current light-emitting diode 930 can be transmitted to the exterior of the hook arm 950. Specifically, the hook arm 950 comprises a recess 951 and an abutting portion 953. An object S is received in the recess 951 when carried by the hook arm 950. In this embodiment, the hook arm 950 may further comprises a reflective surface 952. The reflective surface 952 is formed in the hook arm 950 and opposes the alternating current light-emitting diode 930. The abutting portion 953 is disposed in the base 910 and detachably abuts the actuation switch 921 of the circuit board 920.

Moreover, the alternating current light-emitting diode 930 may be selectively disposed in the base 910 or hook arm 950. In this embodiment, the alternating current light-emitting diode 930 is disposed in the base 910.

Accordingly, the lamp apparatus 901 can be fixed to a wall surface by putting the plug (i.e. plug) 940 in the socket. Moreover, when the plug 940 of the lamp apparatus 901 is put in the socket, the upper surface of the lamp apparatus 901 is coplanar with the wall surface, thereby presenting an aesthetically pleasing appearance. As shown in FIG. 9A, when the hook arm 950 carries no object (i.e. when the hook arm 950 switches to the first position I), the abutting portion 953 thereof separates from the actuation switch 921 of the circuit board 920. At this point, the actuation switch 921 outputs a signal to enable the alternating current light-emitting diode 930 to operate in a first operational mode. In this embodiment, the first operational mode selectively refers to no radiation of the alternating current light-emitting diode 930. In another aspect, as shown in FIG. 9B, when carrying an object S, the hook arm 950 switches (downward) to the second position II by the weight of the object S. At this point, the abutting portion 953 of the hook arm 950 abuts the actuation switch 921 of the circuit board 920, and the actuation switch 921 outputs another signal to enable the alternating current light-emitting diode 930 to operate in a second operational mode. In this embodiment, the second operational mode selectively refers to radiation of the alternating current light-emitting diode 930. In other embodiments, the first operational mode may selectively refer to radiation of the alternating current light-emitting diode 930, and the second operational mode may selectively refer to no radiation of the alternating current light-emitting diode 930.

Accordingly, when the lamp apparatus 901 (or hook arm 950) carries the object S, such as a key, the alternating current light-emitting diode 930 outputs light passing through the base 910 and hook arm 950, thereby highlighting the position of the key.

Moreover, when the lamp apparatus 901 (or hook arm 950) carries the object S, such as a painting, in addition to passing through the base 910 and hook arm 950, the light output from the alternating current light-emitting diode 930 is reflected (downward) by the reflective surface 952 formed in the hook arm 950, irradiating the object S, and further decorating the painting.

Furthermore, the hook arm may be a resilient member, when the object S is removed from the lamp apparatus 901 (or hook arm 950), the hook arm 950 returns to the first position I and the alternating current light-emitting diode 930 operates in the first operational mode, the alternating current light-emitting diode 930 automatically stops radiation, reducing electric power consumption.

Tenth Embodiment

Elements corresponding to those in the ninth embodiment share the same reference numerals.

Figure 11:
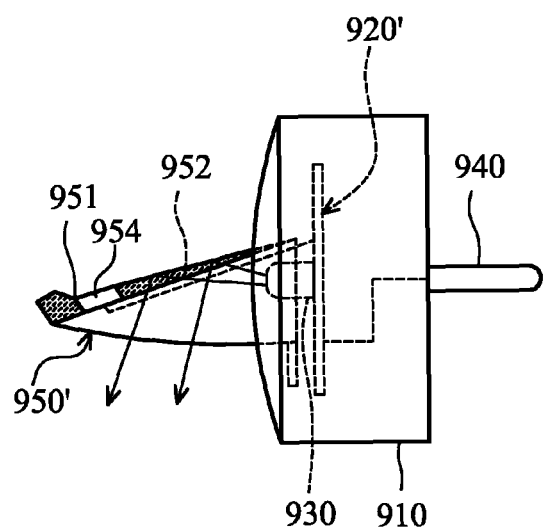
FIG. 11 is a schematic plane view of a lamp apparatus of a tenth embodiment of the invention.

Referring to FIG. 11, a lamp apparatus 903 comprises a base 910, a circuit board 920', a alternating current light-emitting diode 930, a plug 940, and a hook arm 950'.

In this embodiment, the alternating current light-emitting diode 930 is disposed in the base 910. The base 910 is designed to be substantially transparent or semi-transparent. Therefore, the light emitted from the alternating current light-emitting diode 930 could be transmitted to the exterior of the base 910. In other embodiment, the alternating current light-emitting diode 930 may protrude from the surface of the base 910 and not be disposed in the base 910. Therefore, the base 910 may not need to be substantially transparent or semi-transparent to let the light pass through.

The circuit board 920' is disposed in the base 910.

The alternating current light-emitting diode 930 is connected to the circuit board 920'.

The plug 940 is disposed on another surface, opposite to the hook arm 950', of the base 910 and is electrically connected to the circuit board 920'. In this embodiment, the plug 940 can be put in a socket (not shown) to acquire AC electric power. Because the alternating current light-emitting diode 930 doesn't need a rectifier, the overall size of the lamp apparatus 903 can be reduced. In a preferred embodiment, the plug 940 could be a European-type plug, the size of the lamp apparatus 903 can be reduced to fix into the space of the recess of a plug-in on a wall. The outer surface of the base 910 of the lamp apparatus 903 is coplanar with the wall surface to achieve an aesthetically pleasing appearance.

The hook arm 950' is connected to the base 910 and protrudes therefrom. In this embodiment, the hook arm 950' could be substantially transparent or semi-transparent. The light emitted from the alternating current light-emitting diode 930 can be transmitted to the exterior of the hook arm 950'. Specifically, the hook arm 950' comprises a recess 951 and a touch sensor 954. An object S is received in the recess 951 when carried by the hook arm 950'. In this embodiment, the hook arm 950 may further comprises a reflective surface 952. The reflective surface 952 is formed in the hook arm 950' and opposes the alternating current light-emitting diode 930. The touch sensor 954 is electrically connected to the circuit board 920'.

Moreover, the alternating current light-emitting diode 930 may be selectively disposed in the base 910 or hook arm 950'. In this embodiment, the alternating current light-emitting diode 930 is disposed in the base 910.

Accordingly, the lamp apparatus 903 can be fixed to a wall surface by putting the plug (plug) 940 in the socket. Moreover, when the plug 940 of the lamp apparatus 903 is put in the socket, the upper surface of the lamp apparatus 903 is coplanar with the wall surface, thereby presenting an aesthetically pleasing appearance. When the hook arm 950' carries an object (not shown), i.e. when the touch sensor 954 contacts an object, the touch sensor 954 outputs a signal to enable the alternating current light-emitting diode 930 to operate in a first operational mode. In this embodiment, the first operational mode selectively refers to radiation of the alternating current light-emitting diode 930. In another aspect, when the hook arm 950' carries no object, i.e. when the touch sensor 954 separates from the object, the touch sensor 954 outputs another signal to enable the alternating current light-emitting diode 930 to operate in a second operational mode. In this embodiment, the second operational mode selectively refers to no radiation of the alternating current light-emitting diode 930. In other embodiments, the first operational mode may selectively refer to no radiation of the alternating current light-emitting diode 930, and the second operational mode may selectively refer to radiation of the alternating current light-emitting diode 930.

Accordingly, when the lamp apparatus 903 (or hook arm 950') carries the object, such as a key, the alternating current light-emitting diode 930 outputs light passing through the base 910 and hook arm 950', thereby highlighting the position of the key.

Moreover, when the lamp apparatus 903 (or hook arm 950') carries the object, such as a paint, in addition to passing through the base 910 and hook arm 950', the light output from the alternating current light-emitting diode 930 is reflected (downward) by the reflective surface 952 formed in the hook arm 950', irradiating the object, and further decorating the painting.

Furthermore, when the object is removed from the lamp apparatus 903 (or hook arm 950'), the alternating current light-emitting diode 930 automatically stops radiation, thus reducing electric power consumption.

In conclusion, as the disclosed lamp apparatuses with the alternating current light-emitting diodes can operate directly with the AC electric power, no rectifier is needed. Thus, power loss during operation of power rectification is eliminated, enhancing operational efficiency of the lamp apparatuses. Moreover, as no rectifier is needed by the disclosed lamp apparatuses, the size thereof is significantly reduced.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A lamp apparatus, comprising:
 a base;
 a circuit board disposed in the base and comprising an actuation switch;
 a light-emitting diode connected to the circuit board; a plug electrically connected to the circuit board; and
 a hook arm pivoting the base and rotating between a first position and a second position, wherein when an object is hung on the hook arm and the hook arm switches to the first position, the hook arm separates from the actuation switch and the actuation switch enables the light-emitting diode to operate in a first operational mode, and when the hook arm switches to the second position, the hook arm abuts the actuation switch and the actuation switch enables the light-emitting diode to operate in a second operational mode.

2. The lamp apparatus as claimed in claim 1, wherein the base is substantially transparent or semi-transparent.

3. The lamp apparatus as claimed in claim 1, wherein the light-emitting diode is disposed in the base.

4. The lamp apparatus as claimed in claim 1, wherein the light-emitting diode is disposed in the hook arm.

5. The lamp apparatus as claimed in claim 1, wherein the hook arm protrudes from the base.

6. The lamp apparatus as claimed in claim 1, wherein the hook arm is substantially transparent or semi-transparent.

7. The lamp apparatus as claimed in claim 1, wherein the hook arm comprises a reflective surface opposing the light-emitting diode, reflecting light output therefrom.

8. The lamp apparatus as claimed in claim 1, wherein the hook arm further comprises an abutting portion disposed in the base and detachably abutting the actuation switch.

9. The lamp apparatus as claimed in claim 1, wherein the hook arm is a resilient member, and when the object is removed from the hook arm, the hook arm automatically returns to the first position, enabling the light-emitting diode to operate in the first operational mode.

10. The lamp apparatus as claimed in claim 1, wherein the plug comprises a European-type plug.

11. The lamp apparatus as claimed in claim 1, wherein the light-emitting diode operates directly with an alternating current power.

12. A lamp apparatus, comprising:
 a base;

a circuit board disposed in the base;

a light-emitting diode connected to the circuit board;

a plug electrically connected to the circuit board; and a hook arm connected to the base and comprising a touch sensor electrically connected to the circuit board, wherein when contacting an object, the touch sensor enables the light-emitting diode to operate in a first operational mode, and when separating from the object, the touch sensor enables the light-emitting diode to operate in a second operational mode.

13. The lamp apparatus as claimed in claim 12, wherein the base is substantially transparent or semi-transparent.

14. The lamp apparatus as claimed in claim 12, wherein the light-emitting diode is disposed in the base.

15. The lamp apparatus as claimed in claim 12, wherein the light-emitting diode is disposed in the hook arm.

16. The lamp apparatus as claimed in claim 12, wherein the hook arm protrudes from the base.

17. The lamp apparatus as claimed in claim 12, wherein the hook arm is substantially transparent or semi-transparent.

18. The lamp apparatus as claimed in claim 12, wherein the hook arm further comprises a reflective surface opposing the light-emitting diode, reflecting light output therefrom.

19. The lamp apparatus as claimed in claim 12, wherein the plug comprises a European-type plug.

20. The lamp apparatus as claimed in claim 12, wherein the light-emitting diode operates directly with an alternating current power.

\* \* \* \* \*